(12) United States Patent
Curley

(10) Patent No.: US 9,254,182 B2
(45) Date of Patent: Feb. 9, 2016

(54) ORTHODONTIC ARCHWIRE

(71) Applicant: Ormco Corporation, Orange, CA (US)

(72) Inventor: Brandon Curley, Arcadia, CA (US)

(73) Assignee: Ormco Corporation, Orange, CA (US)

(*) Notice: Subject to any disclaimer, the term of this patent is extended or adjusted under 35 U.S.C. 154(b) by 0 days.

(21) Appl. No.: 14/215,263

(22) Filed: Mar. 17, 2014

(65) Prior Publication Data

US 2014/0272754 A1    Sep. 18, 2014

Related U.S. Application Data

(60) Provisional application No. 61/788,990, filed on Mar. 15, 2013.

(51) Int. Cl.
*A61C 7/28*    (2006.01)
*A61C 7/20*    (2006.01)

(52) U.S. Cl.
CPC .. *A61C 7/287* (2013.01); *A61C 7/20* (2013.01)

(58) Field of Classification Search
CPC ............. A61C 7/20; A61C 7/287; A61C 7/30
USPC ................................. 433/8, 10–17, 20–22, 18
See application file for complete search history.

(56) References Cited

U.S. PATENT DOCUMENTS

| | | | |
|---|---|---|---|
| 4,310,579 A | | 1/1982 | Gaydecki |
| 4,582,487 A | * | 4/1986 | Creekmore ....................... 433/8 |
| 4,659,310 A | | 4/1987 | Kottemann |
| 5,344,315 A | | 9/1994 | Hanson |
| 5,380,197 A | * | 1/1995 | Hanson ........................... 433/22 |
| 5,399,088 A | | 3/1995 | Mechley |
| 5,468,147 A | | 11/1995 | Yao |
| 7,354,267 B2 | * | 4/2008 | Vogt ............................... 433/20 |
| 2008/0131831 A1 | | 6/2008 | Abels et al. |
| 2012/0225398 A1 | | 9/2012 | Fallah |

FOREIGN PATENT DOCUMENTS

EP    0420059 B1    3/1994
EP    2519268 A1    11/2012

* cited by examiner

*Primary Examiner* — Edward Moran
(74) *Attorney, Agent, or Firm* — Wood, Herron & Evans, LLP

(57) ABSTRACT

An orthodontic archwire is configured to be inserted into an archwire slot of an orthodontic bracket and is configured to be elastically compressed in a plane that is generally parallel to the plane of the arch form of the archwire. The archwire may include a first exterior surface, a second exterior surface spaced from the first exterior surface, and a resilient element disposed between the first and second exterior surfaces, wherein the resilient element is elastically deformable such that a distance between the first and second exterior surfaces may be decreased upon application of a compressive force on the archwire.

10 Claims, 7 Drawing Sheets

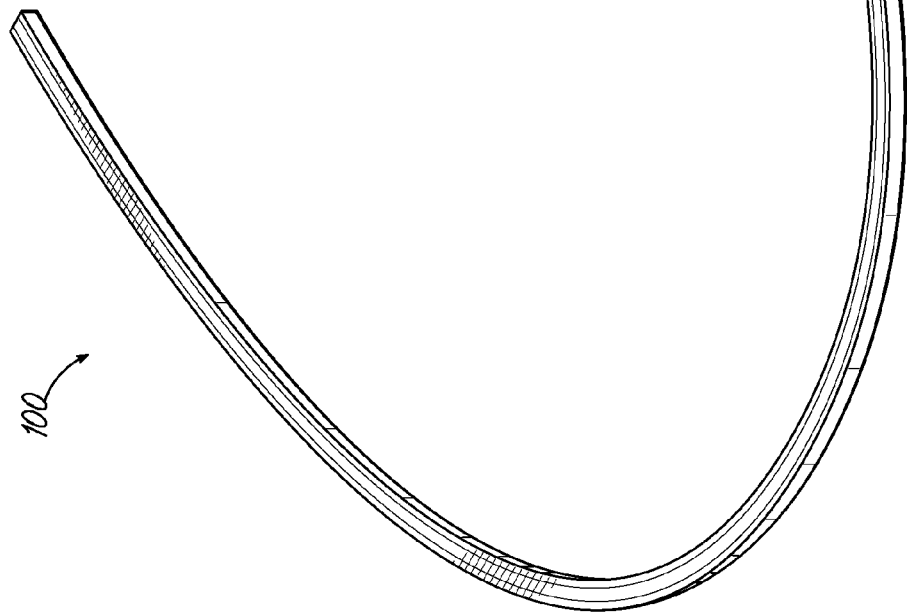
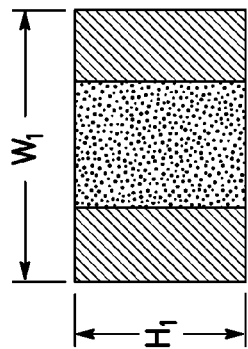
FIG. 1B
FIG. 1A

ORTHODONTIC ARCHWIRE

CROSS REFERENCE TO RELATED APPLICATIONS

This application claims priority to U.S. Provisional Patent Application Ser. No. 61/788,990, filed Mar. 15, 2013, the disclosure of which is incorporated by reference herein in its entirety

TECHNICAL FIELD

The invention relates generally to orthodontic archwires and, more particularly, to compressible orthodontic archwires for use in orthodontic treatment.

BACKGROUND

Orthodontic brackets represent a principal component of corrective orthodontic treatment devoted to improving a patient's occlusion. In orthodontic treatment, an orthodontist affixes brackets to the patient's teeth and engages an archwire into a slot of each bracket. The archwire applies corrective forces that coerce the teeth to move into their aesthetically correct positions. The types of tooth movement desired during orthodontic treatment may vary significantly from the early stage of treatment to the final stage of treatment. The different types of tooth movement desired necessitate fundamentally different approaches for engaging the archwire within the archwire slot.

Self-ligating orthodontic brackets have been developed to eliminate the need for separate ligatures to secure the archwire to the bracket. Self-ligating brackets rely on a movable portion or member, such as a latch or slide, to retain the archwire within the bracket slot.

During the early stages of treatment, a clinician may use an archwire that does not substantially fill the archwire slot. The archwire may, therefore, not be fully seated in the archwire slot during treatment. That is, there may be space between the archwire and two or more opposing surfaces of the archwire slot and/or between the archwire and the movable member. This is often referred to as "passive ligation." As a result, the archwire may slide or move relative to the bracket in the mesial and/or distal directions, in the labial and/or lingual directions, and/or in the occlusal and/or gingival directions during treatment. Thus, passive ligation may allow gross movement of the teeth. Considerable movement between the archwire and the bracket is possible. It will be appreciated that a relatively small archwire, which may be round in cross section, may be used to facilitate passive ligation and thus provide quicker leveling and aligning of the teeth during an initial stage of treatment.

During a later stage of treatment, it may be desirable to more precisely control the orientation of one or more of the teeth. In this regard, the archwire may be forcibly held or fully seated in contact with the archwire slot by the clip and/or optional ligatures to provide control of rotation on the particular tooth. This is often referred to as "active ligation." The clinician may use a relatively large archwire, which may be rectangular as opposed to round, to substantially fill the space within the archwire slot. The larger archwire may then contact both the slot and the clip at the same time to enhance the clinician's control of rotation of and torque on the tooth.

While such self-ligating brackets are generally successful in achieving their intended purpose, there remain some drawbacks. By way of example, in some instances controlling the rotation of the teeth, such as near the finishing stages of orthodontic treatment, can be problematic. While there may be several factors that cause a reduction in rotational control, it is believed that one of the major causes is the loose fit of the archwire within the archwire slot of the bracket when the movable member is closed. When the movable member is closed, the bracket body and the movable member collectively form a closed lumen for capturing the archwire. A close fit between the lumen and the archwire is believed to be important for achieving excellent rotational control during orthodontic treatment.

The close fit between the archwire and the archwire slot when the movable member is closed may be affected by several factors including, for example, the tolerances of the manufacturing process used to form the bracket body and the movable member. When the orthodontic bracket is assembled, the various tolerances may "stack up" so as to provide a relatively loose fit between the archwire and the closed lumen provided by the bracket body and movable member. As noted above, such a loose fit is believed to result in a diminished capacity to control the rotation of the teeth.

Thus, while self-ligating brackets have been generally successful, manufacturers of orthodontic appliances, such as, archwires, continually strive to improve their use and functionality. In this regard, there is a need for orthodontic archwires that provide improved rotational control during orthodontic treatment, such as during the finishing or active stages thereof.

SUMMARY

An orthodontic archwire configured to be inserted into an archwire slot of an orthodontic bracket includes a first exterior surface, a second exterior surface spaced from the first exterior surface, and a resilient element disposed between the first and second exterior surfaces, wherein the resilient element is elastically deformable such that a distance between the first and second exterior surfaces may be decreased upon application of a compressive force on the archwire.

In accordance with the invention, the first exterior surface may be rigid. The second exterior surface may also be rigid. By way of example, the archwire may include a first band that generally defines the first exterior surface and a second band that generally defines the second exterior surface. In an exemplary embodiment, the first and second bands are made of a metal such that the first and second exterior surfaces are rigid. It is expected that the archwire will make contact with the orthodontic bracket along portions of the first and second exterior surfaces. In this way, relative movements between the archwire and archwire slot will be facilitated. The archwire is configured to be oriented relative to the orthodontic bracket such that the first exterior surface is configured to face toward a base surface of the archwire slot and the second surface is configured to face away from the base surface of the archwire slot.

In one embodiment, the resilient element may include a resilient material disposed between the first and second exterior surfaces. By way of example, the resilient material may include a natural or synthetic rubber. In an exemplary embodiment, the archwire includes a first band that defines the first exterior surface, and a second band that defines the second exterior surface and is spaced from the first band, wherein the resilient material is configured as a layer of resilient material that substantially completely fills the space between the first and second bands. This configuration gives the archwire a substantially solid cross-sectional profile. The first and second bands may be formed from a metal.

In another embodiment, the resilient element includes at least one leaf spring. In this embodiment, the at least one leaf spring includes a leg positioned between the first and second exterior surfaces and oriented relative to the first and second exterior surfaces such that an axis of the leg intersects the first and second exterior surfaces in a non-perpendicular manner to define respective first and second acute angles. When the archwire is compressed and the distance between the first and second exterior surfaces decreases, the angle formed between the axis of the leg and the first and second exterior surfaces also decreases. In an exemplary embodiment, the archwire includes a first band that defines the first exterior surface, and a second band that defines the second exterior surface and is spaced from the first band, wherein a plurality of leaf springs are disposed along the length of the archwire each being coupled to the first and second bands.

In yet another embodiment, the resilient element includes at least one v-shaped spring. The at least one v-shaped spring includes a first leg and a second leg joined together at a vertex which is disposed between the first and second exterior surfaces and which defines a vertex axis. In one embodiment, the v-shaped spring may be oriented relative to the first and second exterior surfaces such that the vertex axis extends in a direction that is generally parallel to a longitudinal axis of the archwire. In this embodiment, a first v-shaped spring may be located along a first edge of the first and second exterior surfaces, and a second v-shaped spring may be located along a second edge of the first and second exterior surfaces such that the archwire has a tubular configuration (e.g., having a continuous circumference) for at least a portion of the length of the archwire. In another embodiment, the v-shaped spring may be oriented relative to the first and second exterior surfaces such that the vertex axis extends in a direction that is generally perpendicular to the longitudinal axis of the archwire. In an exemplary embodiment, the archwire includes a first band that defines the first exterior surface, and a second band that defines the second exterior surface and is spaced from the first band, wherein a plurality of v-shaped springs are disposed along the length of the archwire each being coupled to the first and second bands.

In a further embodiment according to the invention, an orthodontic system includes an orthodontic bracket defining an archwire slot configured to receive an archwire therein, and an orthodontic archwire having a first exterior surface; a second exterior surface spaced from the first surface, and a resilient element disposed between the first and second exterior surfaces, wherein the resilient element is elastically deformable such that a distance between the first and second surfaces may be decreased upon application of a compressive force on the archwire. In an exemplary embodiment, the orthodontic bracket is a self-ligating orthodontic bracket. More particularly, the self-ligating bracket is configured as a passive ligation orthodontic bracket wherein the width of the archwire slot is fixed.

In yet another embodiment, a method of ligating an orthodontic archwire to an orthodontic bracket includes providing an orthodontic archwire having a first exterior surface, a second exterior surface spaced from the first surface, and a resilient element disposed between the first and second exterior surfaces, wherein the resilient element is elastically deformable such that a distance between the first and second surfaces may be decreased upon application of a compressive force on the archwire; inserting the orthodontic archwire into an archwire slot of the orthodontic bracket; and contacting the archwire with a rigid portion of the orthodontic bracket to impose a compressive force on the archwire and thereby actively ligate the archwire to the bracket. In an exemplary embodiment, the orthodontic bracket is a self-ligating orthodontic bracket and the step of contacting the archwire with a rigid portion of the orthodontic bracket further comprises moving a movable closure member of the orthodontic bracket to a closed position.

BRIEF DESCRIPTION OF THE DRAWINGS

The accompanying drawings, which are incorporated in and constitute a part of this specification, illustrate embodiments of the invention and, with the summary above together with the detailed description given below, serve to explain the invention.

FIG. 1A is a perspective view of one embodiment of an orthodontic archwire;

FIG. 1B is a cross-sectional view of the archwire shown in FIG. 1A taken along section line 1B-1B;

DETAILED DESCRIPTION

Referring now to FIGS. 1A and 1B, an orthodontic archwire 100 is configured for use in orthodontic treatment. In particular, as is known, archwires are used to correct malpositioned teeth in the human mouth. To do so, archwires are produced in distinct arch forms and are secured to orthodontic brackets, which are attached to each tooth. When human teeth are moved to the arch form defined by the archwire, the teeth are considered to be in aesthetically pleasing orientations. As is shown in FIG. 1A, the archwire 100 is an elongate member that may have an arch form that lies essentially in a flat plane. Neglecting the fact that archwires are three dimensional, the archwire 100 may define an arch form that is curved in two-dimensions. While embodiments of the invention are generally described with reference to a planar archwire, it will be appreciated that embodiments of the present invention may also include curvature of the arch form in a third dimension out of the above-identified plane such that the archwire does not define a flat plane overall. Further, the archwire 100 in the arch form shown is configured to be positioned on a human arch (upper or lower) such that the convex side of the archwire 100 faces in the labial direction and the concave side of the archwire 100 faces in the lingual direction.

With continued reference to FIGS. 1A and 1B, the archwire 100 has a cross-sectional shape. In the exemplary cross section shown in FIG. 1B, the archwire 100 has a first dimension W1 and a second dimension H1 measured generally perpendicular to the first dimension W1. The first dimension W1 may be generally parallel to the plane defined by the archwire 100. By way of example only, and where the archwire has a generally rectangular cross section over at least a portion of its length, the first dimension W1 may represent the width of the archwire 100 in a labial-lingual direction and the second dimension H1 may represent the height of the archwire 100 in an occlusal-gingival direction. As is described in detail below, the archwire 100 is elastically compressible at least in the plane of the arch form.

With reference to FIGS. 1A and 1B, the archwire 100 may be compressible along dimension W1 to a dimension smaller than W1. Compression includes elastic deformation to a smaller dimension in the direction of the applied load so that, upon removal of the load, the archwire 100 reverts to or nearly to dimension W1. Thus, W1 represents a dimension of the archwire 100 in an uncompressed, normal state. It will be appreciated that the dimension H1 may remain the same during compression of the archwire 100 in a plane generally parallel to the plane of the arch form. Embodiments of the invention are not intended to be expandable to a larger dimension than dimension W1 and/or dimension H1, along any particular direction under normal loads observed during orthodontic treatment.

Figure 2A:
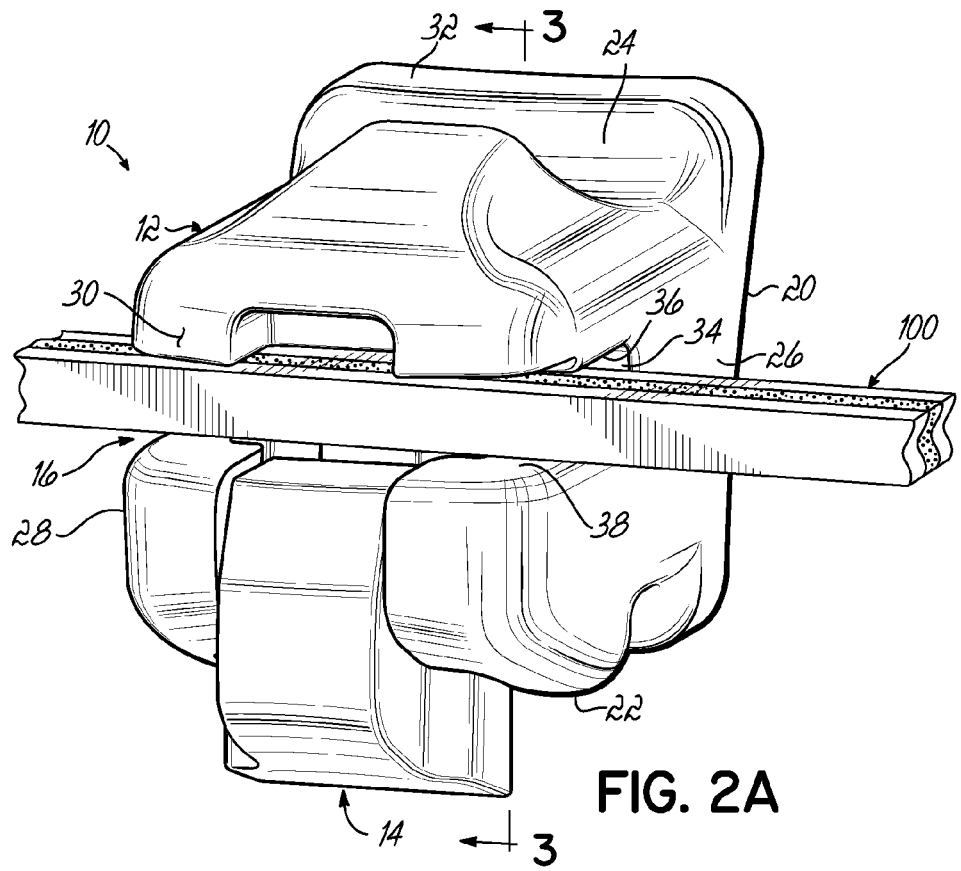
FIG. 2A is a perspective view of an orthodontic archwire inserted into a self-ligating orthodontic bracket in accordance with one embodiment of the present invention with a ligating slide shown in an opened position.
Figure 2B:
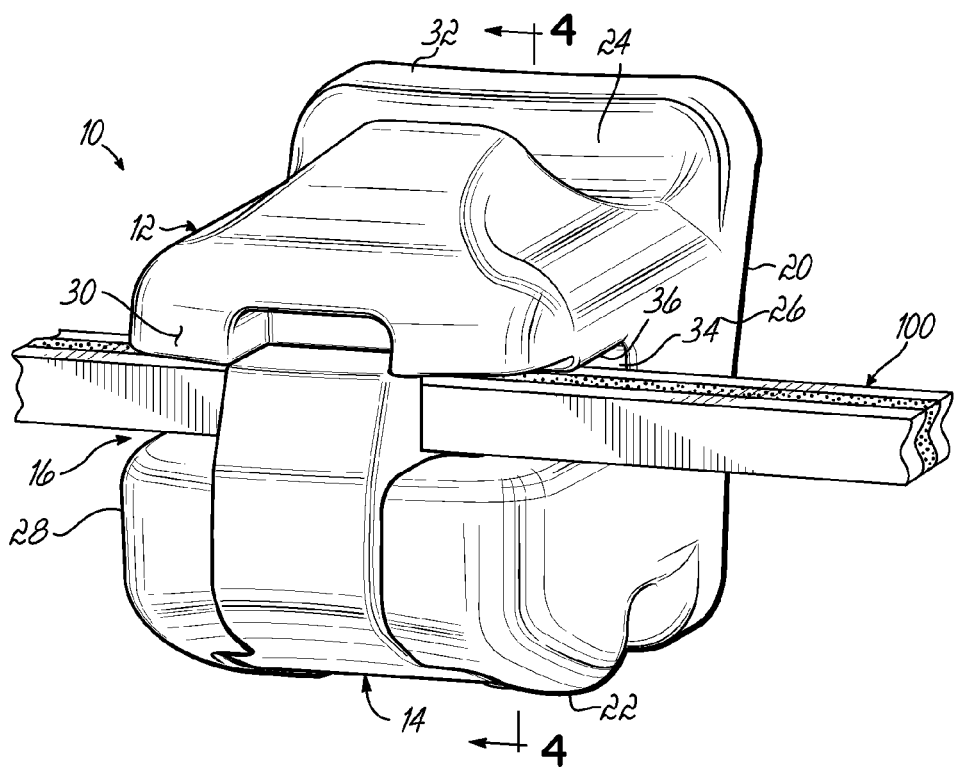
FIG. 2B is a perspective view of the orthodontic archwire and the self-ligating orthodontic bracket shown in FIG. 2A with the ligating slide shown in a closed position.

With reference now to FIGS. 2A and 2B, an orthodontic bracket 10 includes a bracket body 12 and a movable closure member coupled to the bracket body 12. The movable closure member may include a ligating slide 14, as shown, slidably coupled with the bracket body 12. The bracket body 12 includes an archwire slot 16 formed therein adapted to receive the archwire 100 for applying corrective forces to the teeth. As is described more fully below, according to embodiments of the present invention, the archwire 100 is elastically compressible in at least one direction in the plane of the arch form, as is described above, and is configured to fill the archwire slot 16 and be in a resiliently biased condition during treatment. Advantageously, the archwire 100 provides improved rotation control during later stages of treatment in which the clinician desires active ligation.

To that end, and while the orthodontic bracket 10 is fully disclosed in commonly owned U.S. application Ser. No. 12/540,638 filed on Aug. 13, 2009, now U.S. Pat. No. 8,251,696, the disclosure of which is incorporated by reference herein in its entirety, selected features of the bracket 10 are disclosed to more fully explain the archwire 100.

In this regard, the ligating slide 14 is movable between an opened position (FIG. 2A) in which the archwire 100 is insertable into the archwire slot 16, and a closed position (FIG. 2B) in which the archwire 100 is retained within the archwire slot 16. Moreover, while the movable closure member is described herein as a ligating slide, the movable closure member may include other movable structures (e.g., latch, spring clip, door, etc.) that are capable of moving in any appropriate manner between an opened and closed position and generally define a closed lumen for both passive and active ligation.

With continued reference to FIGS. 2A and 2B, when mounted to the labial surface of a tooth carried on the patient's upper jaw, the bracket body 12 has a lingual side 20, an occlusal side 22, a gingival side 24, a mesial side, 26, a distal side 28, and a labial side 30. The lingual side 20 of the bracket body 12 is configured to be secured to the tooth in any conventional manner, for example, by an appropriate orthodontic cement or adhesive or by a band around an adjacent tooth (not shown). The lingual side 20 may further be provided with a pad 32 that defines a bonding base adapted to be secured to the surface of the tooth. The pad 32 may be coupled to the bracket body 12 as a separate piece or element, or alternatively, the pad 32 may be integrally formed with the bracket body 12.

The archwire slot 16 includes a base surface 34 and a pair of opposed slot surfaces 36, 38 projecting labially from the base surface 34. The surfaces 34, 36 and 38 collectively define the archwire slot 16 extending in a mesial-distal direction from the mesial side 26 to the distal side 28. The slot surfaces 36, 38 and the base surface 34 are substantially encapsulated or embedded within the material of the bracket body 12.

Figure 3:
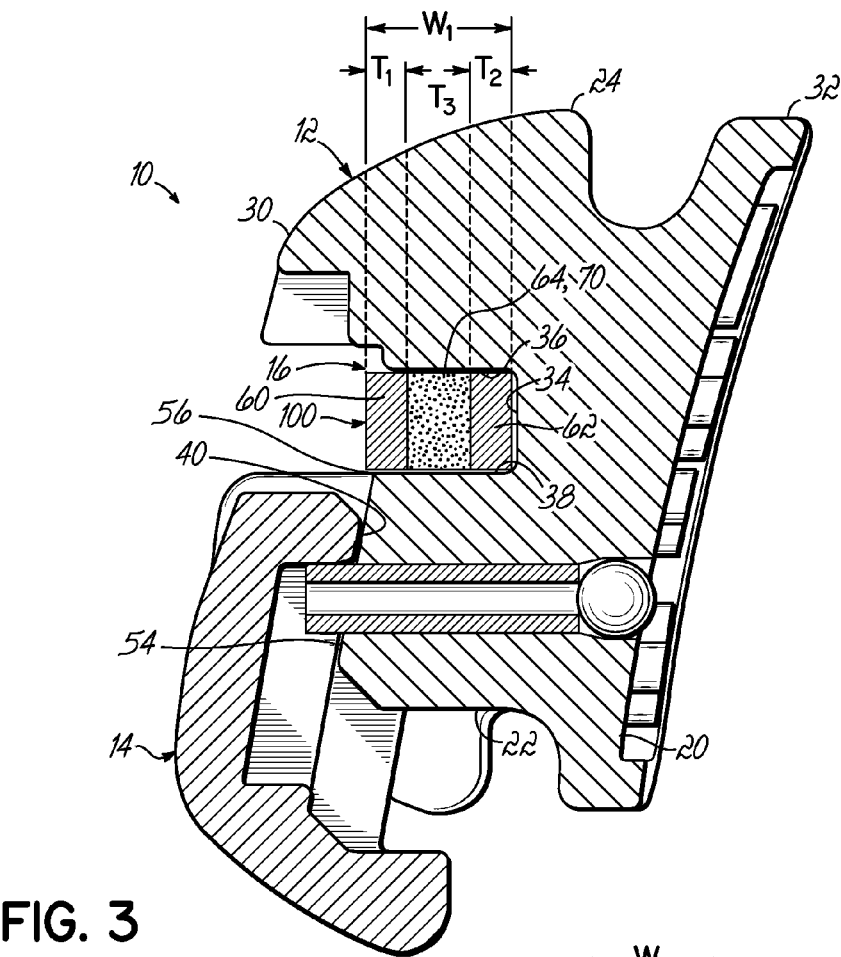
FIG. 3 is a cross-sectional view of the orthodontic archwire and the self-ligating orthodontic bracket shown in FIG. 2A taken generally along line 3-3.

With reference to FIGS. 2A and 3, the archwire slot 16 of the bracket body 12 may be designed to receive the orthodontic archwire 100 in any suitable manner. When the ligating slide 14 is in the opened position, the archwire 100 may be inserted into the archwire slot 16. As shown, the archwire 100 substantially fills the archwire slot 16 in a labial-lingual direction. With regard to the labial-lingual direction, the archwire 100 may extend labially beyond a labially-facing surface 54, which intersects the opposed slot surface 38 to define a labialmost edge 56 of the archwire slot 16. Accordingly, as shown in FIG. 3, the width, W1, in a labial-lingual dimension, which is generally parallel to the plane of the arch form (FIG. 1A) of the archwire 100 is greater than the depth of the archwire slot 16 as defined by the distance measured from the base surface 34 perpendicularly to an extension of the labially-facing surface 54.

Figure 4:
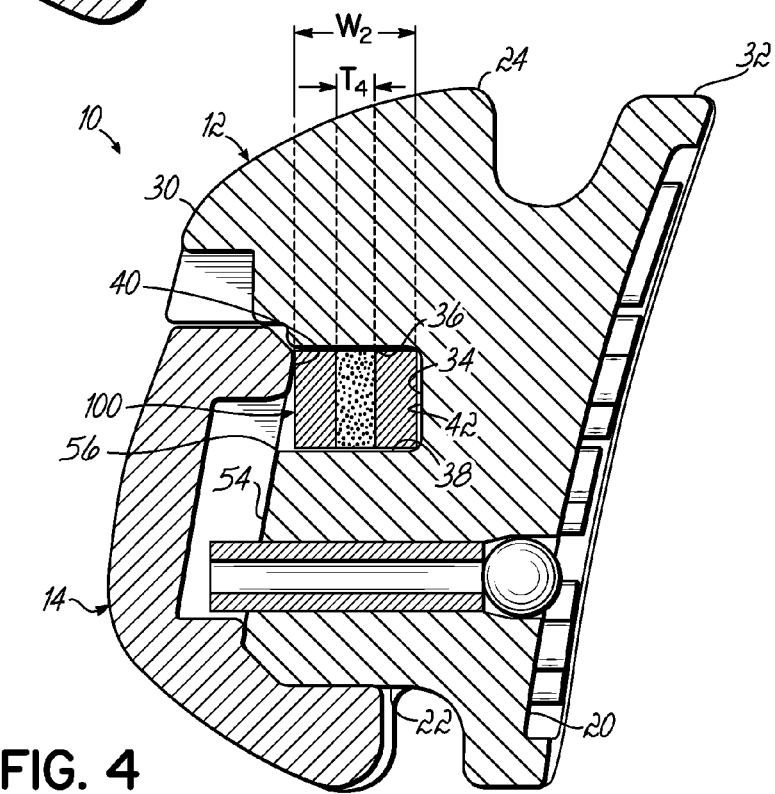
FIG. 4 is a cross-sectional view of the orthodontic archwire and the self-ligating orthodontic bracket shown in FIG. 2B taken generally along line 4-4.

With reference now to FIGS. 2B and 4, the ligating slide 14 may be intentionally moved to the closed position, as shown. When in the closed position, the ligating slide 14 is positioned opposite the base surface 34 and forms a closed lumen 42 that prevents inadvertent removal of the archwire 100 therefrom during treatment. However, in view of the dimension W1, as is described above in conjunction with FIG. 3, the archwire 100 may be compressed to a dimension W2 that is less than W1 when the ligating slide 14 is in the closed position (e.g., compare FIGS. 3 and 4). Compression of the archwire 100 to the dimension W2 may be generally parallel to the plane of the arch form (FIG. 1A). It will be appreciated that the dimension W2 is substantially the same as the corresponding dimension of the closed lumen 42. In one embodiment, W2 is substantially the same dimension as the depth of the archwire slot 16 as is measured from the base surface 34 to the ligating slide 14 at location 40. In other words, the archwire 100 substantially fills the closed lumen 42 in the labial-lingual direction (generally defined as being from the labial side 30 toward the lingual side 20).

Furthermore, the labial-lingual dimension, W1, of the cross-sectional configuration may be greater than the depth of the archwire slot 16 including stack up tolerances often created during manufacturing of the ligating slide 14 and/or the bracket body 12. Stack up tolerances may be unintentional variation in the designed dimensions of the ligating slide 14 and/or bracket body 12. Advantageously, the archwire 100 may therefore eliminate or at least reduce complications or uncertainty in the fit between the archwire 100 and the archwire slot 16 because the archwire 100 may be compressed so as to fit within the actual labial-lingual dimensions present rather than the designed dimensions of the bracket 10.

Furthermore, as is described below, the archwire 100 is compressed by the difference between the dimension W1 (FIG. 3) and the dimension W2 (FIG. 4) and is thus in a compressed state in at least a compressed region between the ligating slide 14 and the archwire slot 16 when the ligating slide 14 is in the closed position. In this regard, while the archwire 100 may be generally compressed along its entire length, during treatment, selected compressed regions may alternate with uncompressed or expanded regions. For example, at regions substantially outside of the compressed zone, the archwire 100 may be expanded. So, during treatment with a plurality of brackets 10, the archwire 100 may be compressed at regions of contact between each ligating slide/bracket and the archwire 100, but the archwire 100 may be generally expanded in regions between adjacent ligating slides/brackets. By expanded it is meant that the archwire 100 is not compressed and has the dimension W1 between brackets 10. Further in this regard, the archwire 100 is not stranded or not multi-stranded or braided of multiple individual filaments, which are capable of being separated so as to result in an expanded overall cross-sectional shape. To the contrary, the cross-sectional shape of archwire 100 may not be expandable to a dimension greater than W1.

With reference to FIGS. 3 and 4, in one embodiment, when the ligating slide 14 is moved from the closed position (FIG. 4) to the opened position (FIG. 3), the archwire 100 is configured to expand from the compressed dimension W2 to the dimension W1. According to embodiments of the present invention, the archwire 100 may be compressed and then expanded repeatedly during the course of orthodontic treatment with the expanded dimension W1 being greater than the dimensions of the closed lumen 42, as described above. Repeated compression and expansion may occur each time the clinician opens the ligating slide 14 to remove and insert the archwire 100.

Additionally, during treatment, the archwire 100 may gradually slide through the closed lumen 42. That is, the bracket 10 may move relative to the archwire 100. To do so, the archwire 100 may gradually compress near one edge of the ligating slide 14 to the dimension W2 as the archwire 100 slides into the closed lumen 42 and expand near the opposing edge of the ligating slide 14 to the dimension W1 as the archwire 100 emerges from the closed lumen 42.

Figure 5:
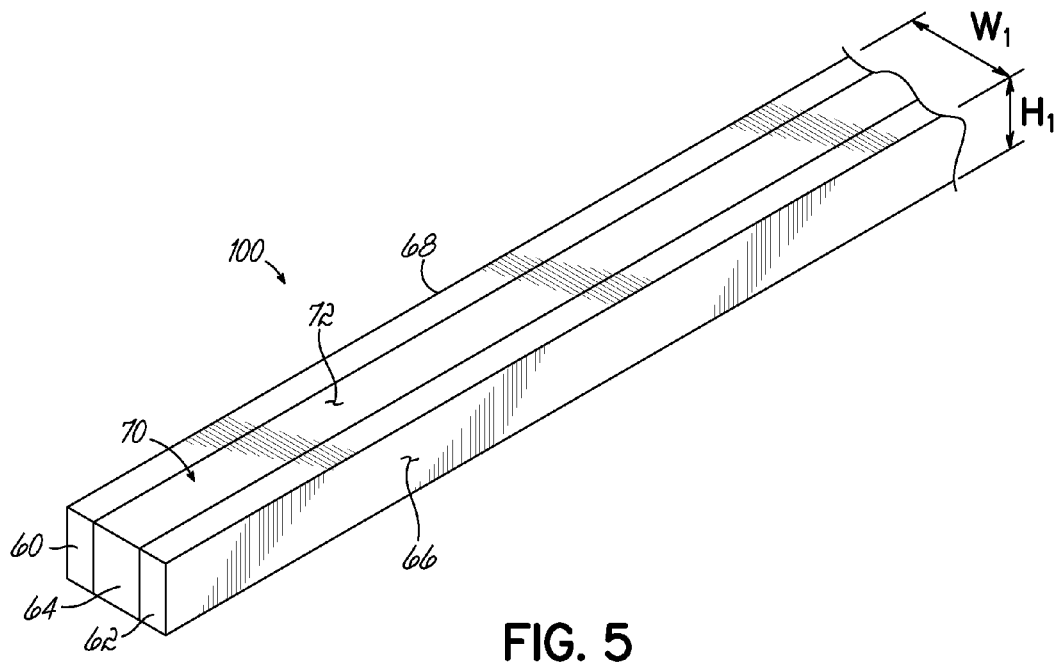
FIGS. 5-15 are perspective views of individual exemplary embodiments of orthodontic archwires according to embodiments of the present invention having differing cross-sectional configurations.

With reference to FIGS. 3 and 5, in one embodiment, the archwire 100 includes opposing outer bands 60, 62 that are separated by an inner band 64. The distance between an outer exterior surface 66 of the band 60 and an outer exterior surface 68 of the band 62 defines the dimension W1. Each of the outer bands 60, 62 defines a thickness. For example, the outer band 60 may have a thickness represented by T1 and the outer band 62 may have a thickness represented by T2. While the thicknesses T1 and T2 may be substantially the same, as shown, embodiments of the present invention are not limited to the thicknesses T1 and T2 being the same. Generally, the outer bands 60, 62 do not change in dimension when the archwire 100 is compressed. In other words, the outer bands 60, 62 and their respective outer exterior surfaces 66, 68 may be generally rigid under the loads experienced by the archwire 100 during installation of the archwire 100 into the bracket 10. This configuration may generally facilitate relative sliding movement of the archwire 100 through the archwire slot 16 in the orthodontic bracket 10.

As is described above, the archwire 100 is configured to be compressible or elastically deformable. In this regard, at least one dimension of the archwire 100 may be reduced or decreased when the ligating slide 14 is moved to the closed position. A portion of the archwire 100 is configured to be compressed in a plane generally parallel to the plane of the arch form during orthodontic treatment. In one embodiment, the inner band 64 is configured to change dimension when the archwire 100 changes dimension between the uncompressed dimension W1 (FIG. 3) and the compressed dimension W2 (FIG. 4). The compression of the archwire 100 is therefore generally in the plane of the arch form of the archwire 100, as shown in FIG. 1A. In particular, the inner band 64 is configured to change dimension by the difference between the expanded dimension W1 and the depth of the archwire slot 16 as measured from the base surface 34 to the labially-facing surface 54, as shown in FIG. 3.

When the archwire 100 is in the expanded state, that is, when the archwire 100 has the dimension W1 and is uncompressed, the inner band 64 may be defined by a dimension T3. Thus, when the archwire 100 is uncompressed in the labial-lingual direction, in one embodiment, the thicknesses T1, T2, and T3 substantially define the dimension W1. By way of example only and not limitation, one or both of the dimensions T1 and T2 may be from about 0.006 inch to about 0.012 inch, and by way of further example, T1 and T2 may be from about 0.008 inch to about 0.010 inch. And, by way of example only, the dimension T3 may be equivalent to at least one of T1 or T2, and by way of further example may be from about 0.006 inch to about 0.012 inch or from about 0.008 inch to about 0.010 inch. It will be appreciated that the dimensions of the archwire slot 16, as set out above, may determine the dimension W1 and/or each of the dimensions T1, T2, and/or T3.

When the archwire 100 is compressed, as is shown in FIG. 4, the dimension of the inner band 64 is reduced from T3 by the difference between W1 and the depth of the archwire slot 16, as set forth above, and is represented by the dimension T4 in FIG. 4. Thus, the dimension T4 is less than T3. Typically, the difference between T4 and T3 is a few thousandths of an inch. By way of example, the difference between the dimension T4 and the dimension T3 may be as little as 0.001 inch or so to about 0.005 inch, and by way of further example, the difference between the dimension T4 and the dimension T3 may be from about 0.003 inch to about 0.005 inch. While specific dimensions for each of the opposing outer bands 60, 62 and the inner band 64 are provided, embodiments of the present invention are not limited to any specific dimension. In this regard, the dimensions of the archwire slot 16 determine the uncompressed dimension W1 and each of the thicknesses T1, T2, and T3.

By way of additional example, and with reference to FIGS. 3 and 4, a standard archwire slot depth dimension may be approximately 0.028 inch. Accordingly, the uncompressed dimension W1 of the archwire 100 may be about 0.030 inch to about 0.032 inch so that the archwire 100 is compressed by about 0.002 inch to about 0.004 inch when the ligating slide 14 is in the closed position. It will be appreciated that standard archwire slot dimensions are nominal dimensions, for example, 0.028 inch, and may be subject to manufacturing tolerances of a few thousandths of an inch. Therefore, a 0.028 inch archwire slot depth may not be exactly 0.028 inch deep because of machining tolerances and the like. In this regard, as was described above, the archwire 100 may be designed taking into account normal manufacturing tolerances. For example, where the manufacturing tolerance is ±0.002 inch, the dimension W1 may be greater than the nominal archwire slot dimension plus the manufacturing tolerance (e.g., 0.028 inch plus 0.002 inch equals 0.030 inch) so that when the ligating slide 14 is moved to the closed position, some compression of the archwire 100 is observed. Advantageously, the archwire 100 fills the full dimension of the archwire slot despite the manufacturing tolerances associated with that particular dimension and provides consistent, predictable torque control.

As described above, in one embodiment, the inner band 64 changes dimension between the normal, expanded state and the compressed state of the archwire 100. To that end, the archwire 100 may include one or more resilient elements 70 generally disposed between the outer exterior surfaces 66, 68. In various embodiments, the one or more resilient elements may extend between and secure the outer band 60 to the opposing outer band 62. The resilient elements 70 at least partially define the inner band 64.

For example, and with reference to FIG. 5, in one embodiment, the outer band 60, the outer band 62, and the inner band 64 are layered in a sandwich-type configuration. Thus, the archwire 100 may have a substantially solid cross-sectional profile. The thicknesses of each of the outer bands 60, 62 plus the inner band 64 determine the width dimension W1 generally parallel to the plane of the arch form and any of the occlusal-gingival dimensions of the outer bands 60, 62 and/or inner band 64 determine the height H1 of the archwire 100.

In the embodiment shown, the opposing outer bands 60, 62 are or include metal. For example, each of the outer bands 60, 62 may be a metal strip. The metallic outer bands 60, 62 may be secured together by the resilient element 70 of the inner band 64. It will be appreciated that, because the opposed outer bands 60, 62 generally define the outer surfaces 66, 68 of the archwire 100, the archwire 100 may have similar wear characteristics as a conventional archwire made of the same metal. In that regard, the outer bands 60, 62 may be a stainless steel alloy, a Nickel Titanium (NiTi) alloy, a Copper Nickel Titanium (CuNiTi) alloy, or a Copper Aluminum Nickel (CuAlNi) alloy. Thus, the outer bands 60, 62 and their exterior surfaces 66, 68 provide relatively hard and low friction sliding surfaces.

The resilient element 70 may be a layer 72 of resilient material, such as, natural or synthetic rubber. The resilient material in the layer 72 is compressible, but resiliently biases the outer band 60 away from the outer band 62 when so compressed. The archwire shown in FIG. 5 may be made by adhering the layer 72 to each of the outer bands 60, 62 with an appropriate adhesive or by inserting pins (not shown) through each of the outer bands 60, 62 and through the layer 72. Those of ordinary skill in the art may recognize other techniques for coupling the layer 72 to each of the outer bands 60, 62.

Figure 6:
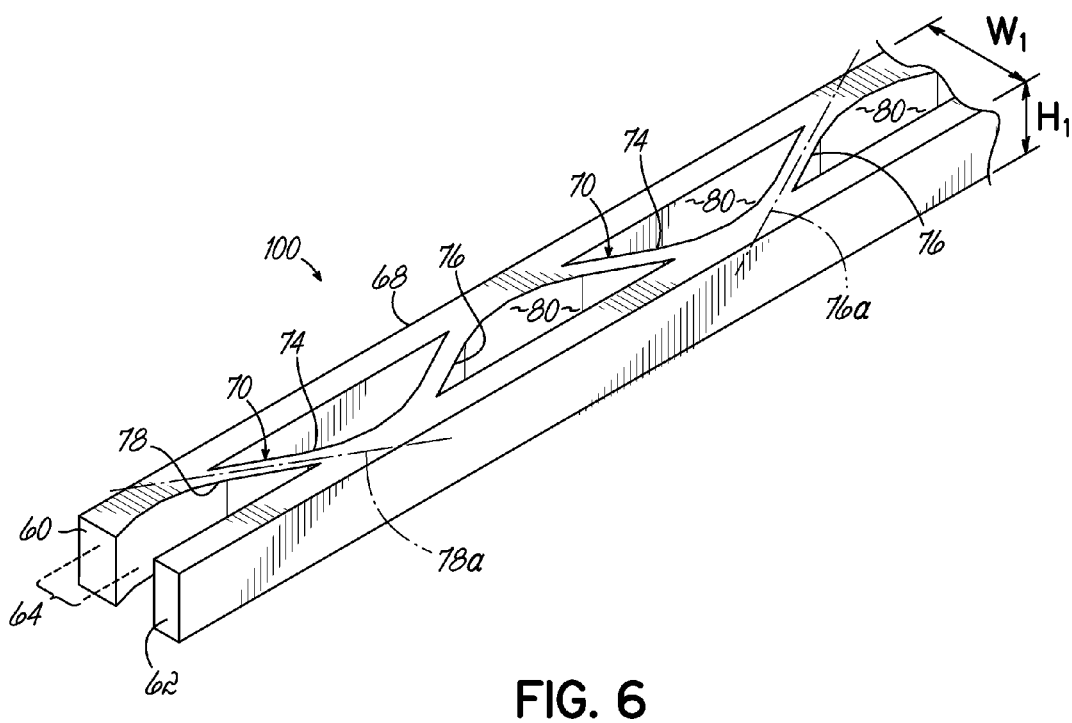

In one embodiment, and with reference to FIG. 6, the inner band 64 may include resilient elements 70 in the configuration of one or more leaf springs 74. The outer bands 60, 62 plus the uncompressed leaf springs 74 define the width W1 of the archwire 100 generally parallel to the plane of the arch form (FIG. 1).

As shown, the leaf spring 74 may include leg 76 or 78 that connect the outer band 60 to the outer band 62 and defines a compression space 80 therebetween. Each of the legs 76, 78 generally defines a leg axis 76a, 78a and is oriented relative to exterior surfaces 66, 68 (and outer bands 60, 62) such that the leg axes 76a, 78a intersect the exterior surfaces 66, 68 in a non-perpendicular manner so as to define an acute angle therebetween.

When the archwire 100 is compressed, the acute angle decreases in value or magnitude and the width of the archwire 100 at this location is reduced to a dimension less than W1. Although not shown, it would be appreciated that the compression space 80 is reduced upon compression of the outer band 60 toward the outer band 62. Thus, compression space 80 allows the dimension of the inner band 64 to be reduced while the leaf springs 74 resiliently bias the outer band 60 away from the outer band 62. With reference to FIGS. 2A and 2B, when compressed the ligating slide 14 may be closed so as to capture the archwire 100 therein at which time the archwire 100 expands to fill the available space created by the closed lumen 42. By way of example only and not limitation, the thickness of one or both legs 76, 78 may be from about 0.001 inch to about 0.010 inch, and by way of further example the thickness of one or both legs may be from about 0.003 inch to about 0.008 inch. The thicknesses of each leg 76, 78 may depend upon the material from which the archwire 100 is made, the amount of compression desired, and the force required to compress the archwire 100, among other factors. Furthermore, the thicknesses of legs 76, 78 and/or the outer bands 60, 62 may change over the length of the archwire 100. Thus, the stiffness of the archwire 100 may similarly change over the length of the archwire 100.

Similar to the embodiment shown in FIG. 5, the archwire 100 shown in FIG. 6 may include outer bands 60, 62 of metal. The leaf springs 74 may also be made of metal and be welded or brazed to the opposed outer bands 60, 62.

Figure 7:
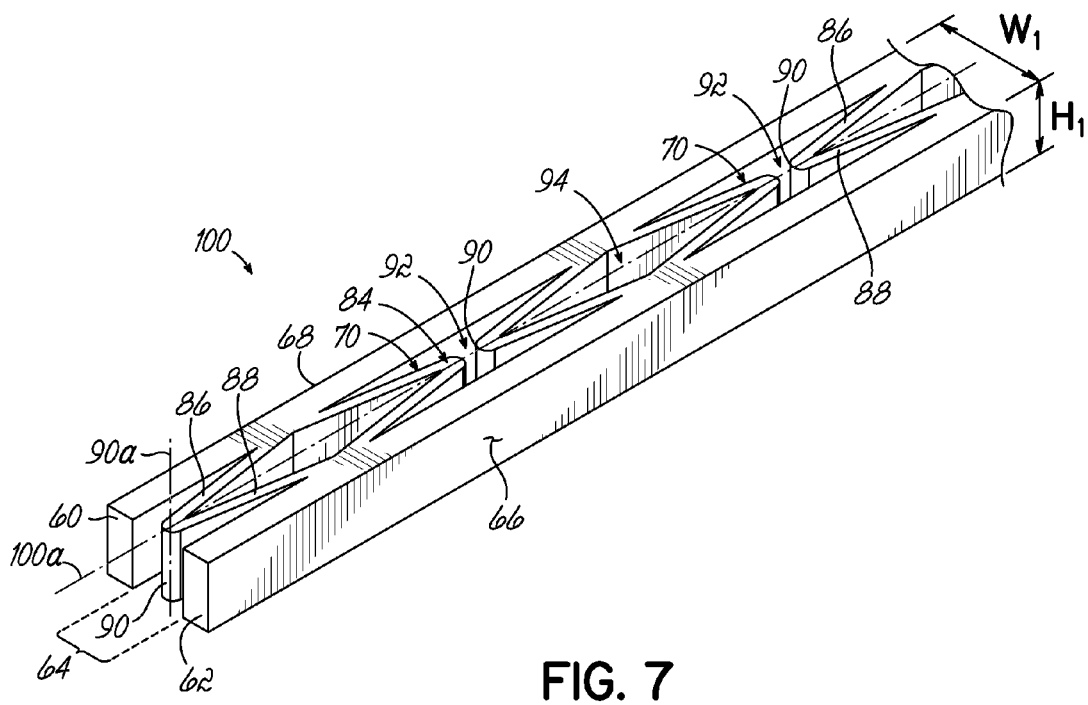

In one embodiment, and with reference to FIG. 7, the inner band 64 may include resilient elements 70 in the configuration of one or more v-shaped springs 84 disposed between the exterior surfaces 66, 68. In one embodiment, the v-shaped springs may connect the outer band 60 to the outer band 62. As shown, each v-shaped spring 84 includes legs 86, 88 joined together at vertex 90 that remain disposed between the outer bands 60, 62 and exterior surfaces 66, 68. In this embodiment, one leg 86 is coupled to the first band 60 and the other leg 88 is coupled to the second band 62. The v-shaped spring 84 is oriented relative to the exterior surfaces 66, 68 such that the legs 86, 88 generally extend along the longitudinal axis 100a of the archwire, and a vertex axis 90a extends in a direction generally perpendicular to the longitudinal axis 100a of the archwire 100. Adjacent v-shaped springs 84 define compression space 92 and compression space 94.

As with the archwire 100, shown in FIG. 6, compression of the archwire 100 brings the legs 86, 88 of the v-shaped spring 84 together reducing the vertex angle of the spring and reducing the compression spaces 92, 94. This, in turn, reduces the dimension of the inner band 64 and allows the outer band 60 to approach the outer band 62. Overall, the width of the archwire 100 is reduced to a dimension less than the dimension W1 upon compressing the inner band 64. During compression, the leg 86 and the leg 88 approach one another, but resiliently bias the outer bands 60, 62 away from each other so that, when the compressive load is removed, the archwire 100 fills the closed lumen 42 (FIG. 4). By way of example only and not limitation, the thickness of one or both legs 86, 88 may be from about 0.001 inch to about 0.008 inch, and by way of further example the thickness of one or both legs may be from about 0.003 inch to about 0.005 inch. The thicknesses of each leg 86, 88 may depend upon the material from which the archwire 100 is made, the amount of compression desired, and the force required to compress the archwire 100, among other factors. Furthermore, the thicknesses of legs 86 and 88 and/or the outer bands 60, 62 may change over the length of the archwire 100. Thus, the stiffness of the archwire 100 may similarly change over the length of the archwire 100.

Similar to the embodiment shown in FIG. 5, the archwire 100 shown in FIG. 7 may include outer bands 60, 62 of metal. The v-shaped springs 84 may also be made of metal and be welded or brazed to the opposed outer bands 60, 62.

The archwire 100, as shown in FIGS. 6 and 7, may be made by extrusion techniques known in the art. Alternatively, the archwire 100 could be grown from a metallic single crystal, such as, of single crystal CuAlNi. Other techniques may include direct-metal manufacturing techniques, such as direct-metal laser sintering (DMLS) and selective laser sintering (SLS), and a selective electroplating process, which is commercially available from Microfabrica, Inc., Van Nuys, Calif.

Figure 8:
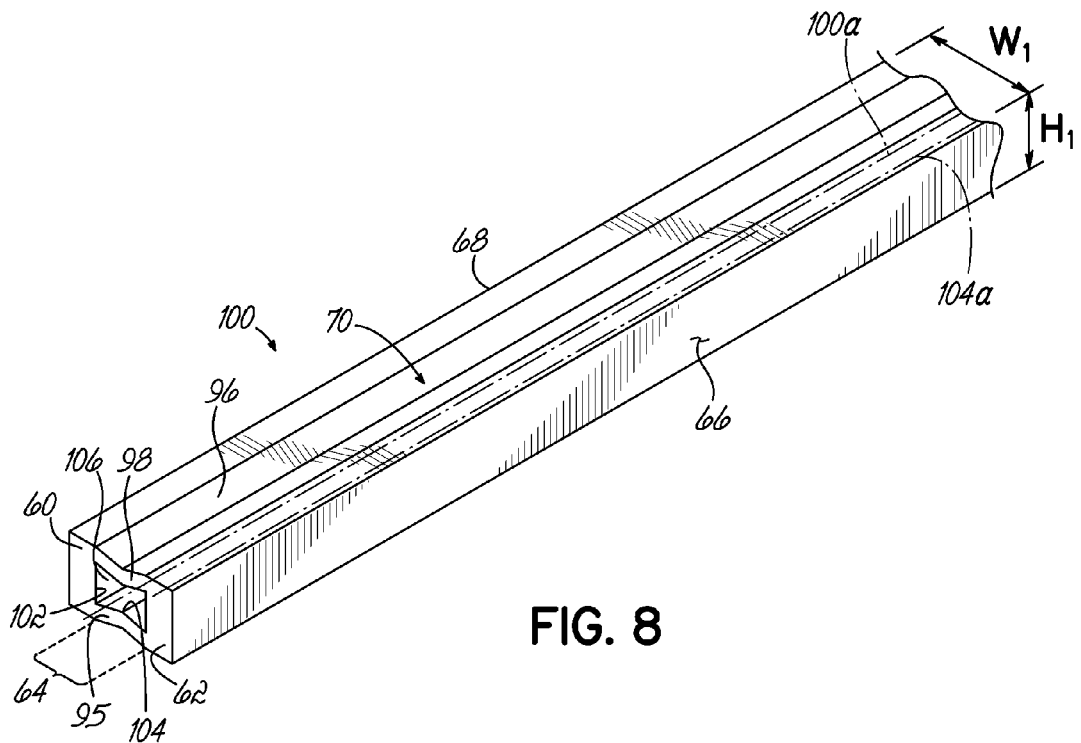

In one embodiment, and with reference to FIG. 8, the inner band 64 may include resilient elements 70 in the configuration of a pair of opposing elongated v-shaped springs 95, 96. As shown, the elongated v-shaped springs 95, 96 extend from the outer band 60 to the outer band 62 so as to form a tubular configuration. Each of the elongated v-shaped springs 95, 96 includes legs 98, 102 joined at a vertex 104 that remain disposed between the exterior surfaces 66, 68. The first v-shaped spring 95 has a first leg 98 that couples to outer band 60 at an edge thereof and a second leg 102 that couples to outer band 62 at an edge thereof. Similarly, the second v-shaped spring 96 has a first leg 98 that couples to outer band 60 at an edge thereof, and a second leg 102 that couples to outer band 62 at an edge thereof. The v-shaped springs 95, 96 are oriented relative to the exterior surfaces 66, 68 such that the legs 98, 102 generally extend in a direction perpendicular to the longitudinal axis 100a of the archwire, and the vertex 104 defines a vertex axis 104a that extends in a direction generally parallel to the longitudinal axis 100a of the archwire 100. A compression space 106 is defined by the outer band 60, the elongated v-shaped springs 95, 96, and the outer band 62.

Compression of the archwire 100 brings the legs 98, 102 of the v-shaped springs 95, 96 together reducing the vertex angle of the springs and reducing the compression space 106. This, in turn, reduces the dimension of the inner band 64 and allows the outer band 60 to approach the outer band 62. Overall, the dimension of the archwire 100 is reduced from the dimension W1 upon compressing the v-shaped springs 95, 96.

During compression, the opposing vertices 104 of the opposing elongated v-shaped springs 95, 96 approach one another in an accordion-like manner as the compression space 106 is reduced. But, the opposing elongated v-shaped springs 95, 96 resiliently bias the outer bands 60, 62 away from one another so that, when the archwire 100 is inserted into the archwire slot 16, the ligating slide 14 closed, and the compressive load is removed, the archwire 100 fills the closed lumen 42 (FIG. 4). By way of example only and not limitation, the thickness of one or both legs 98, 102 may be from about 0.001 inch to about 0.008 inch, and by way of further example the thickness of one or both legs may be from about 0.003 inch to about 0.005 inch. The thickness of each leg 98, 102 may depend upon the material from which the archwire 100 is made, the amount of compression desired, and the force required to compress the archwire 100, among other factors.

Similar to the embodiment shown in FIG. 5, the archwire 100 shown in FIG. 8 may include outer bands 60, 62 of metal. The v-shaped springs 95, 96 may also be made of metal and be welded or brazed to the opposed outer bands 60, 62. Alternatively, the archwire 100, as shown in FIG. 8, may be manufactured with a die by conventional extrusion methods.

With reference now to FIGS. 9-12, additional configurations of the archwire 100 are shown. In each, the cross-sectional configuration is generally rectangular and is elastically compressible along at least the dimension W1, which is generally parallel to the plane of the arch form (FIG. 1A). With this configuration, the archwire 100 may substantially fill the archwire slot 16 (FIGS. 3 and 4) in the occlusal-gingival direction and be compressible in the labial-lingual direction so as to completely fill the closed lumen 42 in the plane of the arch form, that is, in the labial-lingual direction.

Figure 9:
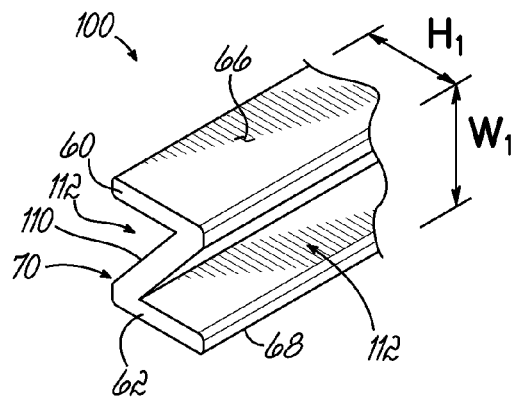

For example, with reference to FIG. 9, the archwire 100 has a z-shaped configuration and is generally rectangular in cross section having a dimension W1 generally parallel to the plane of the arch form of the archwire 100, as is shown in FIG. 1A. The archwire 100 has a dimension H1 generally perpendicular to the dimension W1. The z-shaped configuration may include the resilient element 70 in the form of a leg 110 that joins the outer bands 60, 62 at opposing edges and defines a pair of open compression spaces 112 to either side of the leg 110. Compression of the archwire 100 reduces the volume of the compression spaces 112 by elastically bending the leg 110 at or near each of the locations at which the leg 110 joins the corresponding outer band 60 and 62. As the opposing bands 60, 62 approach one another, the archwire 100 is compressed to a dimension less than the dimension W1. When the archwire 100 is compressed and inserted into the archwire slot 16 (FIG. 2A), the leg 110 resiliently biases the outer bands 60, 62 away from one another so that, when the ligating slide 14 is closed and the compressive load is removed, the archwire 100 fills the closed lumen 42 (FIG. 4) and the archwire 100 is continuously biased toward the uncompressed z-shaped configuration having dimension W1.

Figure 10:
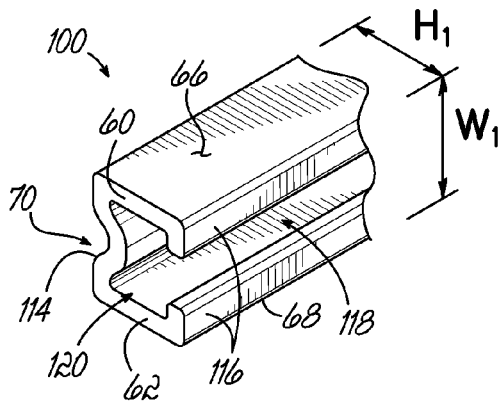

In one embodiment, and with reference to FIG. 10, the archwire 100 may be configured with a sigma-shape in which the outer bands 60, 62 are joined by the resilient element 70 in the configuration of a generally u-shaped spring 114. Shoulder extensions 116 extend from the outer bands 60, 62 opposite the u-shaped spring 114 and define a slot 118 between the extensions 116. The outer bands 60, 62, u-shaped spring 114, and extensions 116 generally enclose a compression or hollow space 120 within the archwire 100. Compression of the archwire 100 reduces the volume of the compression space 120 by resiliently deforming the u-shaped spring 114. The extensions 116 also approach one another so as to reduce the size of the slot 118. As the opposing bands 60, 62 approach one another, the archwire 100 is reduced to a dimension that is less than dimension W1. When the archwire 100 is compressed, the u-shaped spring 114 resiliently biases the outer bands 60, 62 away from one another so that, when the archwire 100 is inserted into the archwire slot 16 and the compressive load is removed, the archwire 100 fills the closed lumen 42 (FIG. 4) and the archwire 100 is continuously biased toward the uncompressed z-shaped configuration.

Figure 11:
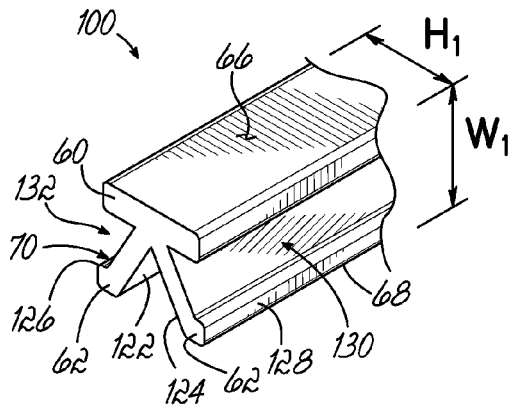

In one embodiment, and with reference to FIG. 11, the archwire 100 may be configured with a generally pi-shape in which the outer band 60 defines one exterior surface 66 of the archwire 100. Legs 122, 124 extend from the outer band 60. Each leg 122, 124 may include a corresponding tab 126, 128. Collectively, the legs 122, 124 and, if present, tabs 126, 128 form the band 62. Legs 122, 124 define open compression spaces 130, 132. Compression of the archwire 100 reduces the volume of the compression spaces 130, 132 by resiliently deforming each leg 122, 124 at or near the band 60. As the opposing bands 60, 62 approach one another, the archwire 100 is reduced to a dimension that is less than dimension W1. When the archwire 100 is compressed, the legs 122, 124 resiliently bias the outer bands 60, 62 away from one another so that, when the archwire 100 is inserted into the archwire slot 16 and the compressive load is removed, the archwire 100 fills the closed lumen 42 (FIG. 4) and the archwire 100 is biased toward the uncompressed pi-shaped configuration.

Figure 12:
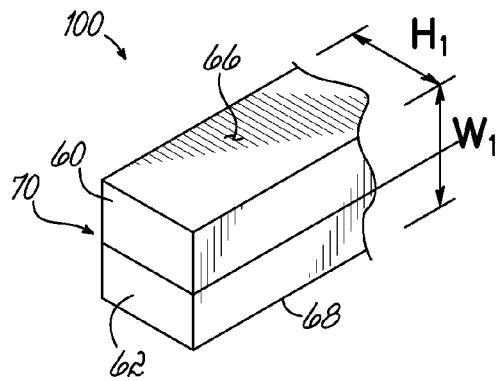

In one embodiment, and with reference to FIG. 12, the archwire 100 may include two bands secured to one another in a bilayer-type archwire. In the exemplary embodiment shown, the archwire 100 may include outer band 60 secured directly to outer band 62. That is, nothing separates the outer bands 60, 62 from one another. In contrast to a three-layered cross section (FIG. 5), in one embodiment, one of the outer bands 60, 62 of the archwire 100 shown in FIG. 12 is configured as the resilient element 70 and the other is of a rigid material. Compression of the archwire 100 may reduce the volume of the resilient element 70 by resiliently deforming the corresponding band 60, 62. In the embodiment in which the outer band 60 is the resilient element 70, compressing the resilient band 60 reduces the dimension of the archwire 100 in a direction that is generally parallel to the plane of the arch form. As the opposing surfaces 66, 68 approach one another, the archwire 100 is reduced to a dimension that is less than dimension W1. When the archwire 100 is compressed, the resilient band 60 resiliently biases the outer surfaces 66, 68 away from one another so that, when the archwire 100 is inserted into the archwire slot 16 and the compressive load is removed, the archwire 100 fills the closed lumen 42 (FIG. 4) and the archwire 100 is biased toward the uncompressed configuration having the dimension W1.

Figure 13:
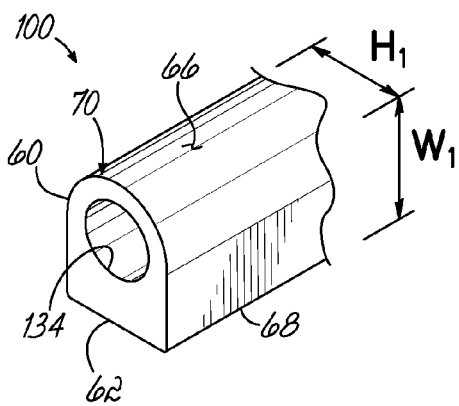
Figure 14:
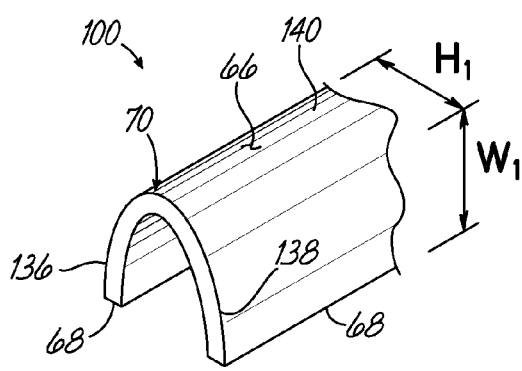
Figure 15:
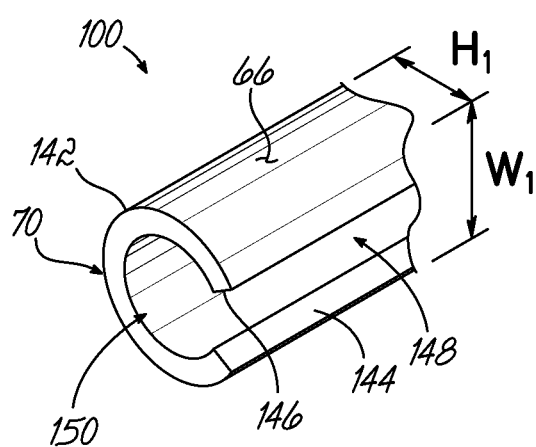

While the archwires according to embodiments of the invention may generally define a rectangular cross-sectional profile (e.g., the embodiments shown in FIGS. 5-12 are generally rectangular cross-sectional profiles), embodiments of the present invention are not limited to these profiles. For example, as is shown in FIGS. 13-15, embodiments of the archwire 100 may have a non-rectangular cross-sectional profile. However, each archwire has an uncompressed, normal configuration (as shown) and a compressed configuration in which a dimension generally parallel to the plane of the arch form is less than an uncompressed dimension W1.

For example, with reference to FIG. 13, the archwire 100 may include at least one curved exterior surface and so deviate from a rectangular cross-sectional configuration due to the curvature of that exterior surface. In the exemplary embodiment shown, the outer band 60 is curved in a circular cylinder so as to form a curved outer surface 66. The outer band 60 in conjunction with a bore 134 forms the resilient element 70. The bore 134 may extend the entire length of the archwire 100 or a portion thereof. While not shown, during compression, the outer band 60 may resiliently deform into the bore 134. In this regard, the outer band 60 may flatten out. As the outer band 60 is resiliently deformed toward the outer band 62, the volume of the bore 134 may also be reduced. The archwire 100 may therefore be reduced in a dimension generally parallel to the dimension W1 and in a direction that is generally parallel to the plane of the arch form. When the archwire 100 is compressed, the outer band 60 is continuously resiliently biased in the plane of the archwire 100 so that, when the archwire 100 is inserted into the archwire slot 16 and the compressive load is removed, the archwire 100 fills the closed lumen 42 (FIG. 4).

With reference now to the embodiment shown in FIG. 14, the archwire 100 may be described as a sheet of material formed in a U-shape. This embodiment of the archwire 100 deforms in a similar manner as that described above with respect to the archwire 100 of FIG. 13. The archwire 100 may include an occlusal free end 136 and a gingival free end 138. The free ends 136, 138 collectively define the outer surfaces 68. While not shown, during compression, the outer surface 66 may flatten out. That is, when a compressive force is applied at apex 140 of the outer surface 66, the outer surface 66 may flatten at the location at which the compressive load is applied. The archwire 100 may then be deformed from a smoothly curved U-shaped configuration toward a more rectangular or boxy U-shape as the outer surface 66 resiliently flattens under the applied load. While not shown, the free ends 136, 138 may also move away from one another though the surfaces 36, 38 of the archwire slot 16 may restrict the extent to which the free ends 136, 138 move.

Overall, the archwire is reduced in dimension in at least a direction generally parallel to the plane of the arch form. The compressed dimension measured between the outer surfaces 66 and 68 is less than the dimension W1. However, the archwire 100 may expand in a direction that is perpendicular to the plane of the arch form. In other words, when the archwire 100 is compressed within the closed lumen 42, the dimension perpendicular to the plane of the arch form may be greater than the uncompressed dimension H1 and may completely fill the occlusal-gingival width of the archwire slot 16 as measured between the surface 36 and the surface 38 (FIG. 4). When the archwire 100 is compressed and the archwire 100 is inserted into the archwire slot 16 and then the compressive load is removed, the archwire 100 fills the closed lumen 42.

With reference to FIG. 15, in one embodiment of the invention, the archwire 100 has a circular C-shaped body 142 including opposing free ends 144, 146 that define a longitudinal slot 148 that may extend along the longitudinal length of the archwire 100 or only along selected portions thereof. The body 142 defines a bore or compression space 150 within the archwire 100. When a compressive load is applied to the outer surface 66, the free ends 144, 146 approach one another and the volume of the compression space 150 is reduced as the body 142 resiliently deforms. The archwire 100 may therefore be reduced in a dimension generally parallel to the dimension W1 and in a direction that is generally parallel to the plane of the arch form. The archwire 100 may also be reduced in a dimension generally parallel to the dimension H1 and in a direction that is perpendicular to the plane of the arch form. When the archwire 100 is compressed, the body 142 is resiliently biased in the plane of the archwire 100 so that, when the archwire 100 is inserted into the archwire slot 16 and the compressive load is removed, the archwire 100 fills the closed lumen 42 (FIG. 4).

The archwires shown and described in connection with FIGS. 9-15 may be manufactured in a similar manner as the archwires shown and described in connection with FIGS. 5-8. Furthermore, it will be appreciated that the magnitude of the compressive load required to achieve a predetermined level of elastic compression may be selected by changes to the thicknesses of the bands and/or resilient elements. The archwires 100 as described herein may have some benefits during orthodontic treatment. For example, active ligation of orthodontic archwires is typically achieved by incorporating some type of resilient member into the orthodontic brackets. This often results in complex bracket designs with a relatively high cost. In accordance with embodiments of the present invention, the resilient aspect generally required for active ligation is incorporated into the archwire itself instead of the orthodontic bracket. The associated costs with such a design may be reduced as compared to the complex and expensive designs of many active ligation orthodontic brackets. Additionally, by incorporating the active ligation aspect into the archwire instead of the bracket, most passive bracket designs may be made active in a simple and straightforward manner. In this regard, the orthodontist may replace a conventional archwire with an archwire as disclosed herein to turn a passive ligation orthodontic system into an active ligation orthodontic system.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in any combination depending on the needs and preferences of the user.

What is claimed is:

1. A method of ligating an orthodontic archwire to a self-ligating orthodontic bracket, the self-ligating orthodontic bracket having a bracket body including a pair of opposed slot surfaces projecting from a base surface to define an archwire slot and a movable member, the archwire slot and the movable member collectively define a closed lumen, the method comprising:

securing the self-ligating orthodontic bracket to the tooth;
    inserting the orthodontic archwire into the archwire slot against the base surface;

forcing the archwire against the base surface with an applied force to reduce a dimension of the archwire in the direction of the applied force;

closing the movable member to form the closed lumen; and removing the applied force allowing the dimension of the archwire to expand to fill the closed lumen and to remain partially elastically compressed between the base surface and the movable member during orthodontic treatment.

2. A method of orthodontic treatment with an orthodontic archwire having a U-shape that generally lies in a plane and has a cross-sectional shape with a first dimension measured generally parallel to the plane and a second dimension measured perpendicular to the first dimension and a self-ligating orthodontic bracket including a pair of opposed slot surfaces extending from a base surface to define an archwire slot and a movable member movable between an opened position and a closed position, the method comprising:

securing the self-ligating orthodontic bracket to a tooth of a patient;

inserting the orthodontic archwire into the archwire slot, the first dimension being greater than a dimension between the base surface of the archwire slot and the movable member in the closed position;

compressing the orthodontic archwire from the first dimension to a third dimension that is less than the dimension between the base surface and the movable member in the closed position; and while compressing the orthodontic archwire, moving the movable member to the closed position.

3. The method of claim 2, wherein compressing includes forcing a first outer band of the archwire toward a second outer band of the archwire to thereby compress a resilient member between the first outer band and the second outer band.

4. The method of claim 3, wherein compressing includes reducing a thickness dimension of a layer of the resilient member.

5. The method of claim 4, wherein after compressing the archwire, the resilient member biases at least one of the first and second outer bands in a direction toward the first dimension.

6. The method of claim 2, wherein compressing the archwire changes a cross-sectional shape of the archwire.

7. The method of claim 2, wherein compressing the archwire includes compressing the first dimension in a labial-lingual direction.

8. The method of claim 7, wherein compressing the archwire does not substantially change the second dimension.

9. The method of claim 2, wherein compressing the archwire reduces the third dimension by as little as 0.001 inch to about 0.005 inch less than the first dimension.

10. The method of claim 2, wherein compressing the archwire includes compressing from the first dimension of about 0.030 inches to about 0.032 inches.

* * * * *